United States Patent [19]
Glass et al.

[11] Patent Number: 5,723,294
[45] Date of Patent: Mar. 3, 1998

[54] METHODS FOR DETECTION AND DISCRIMINATION OF MULTIPLE ANALYTES USING FLUORESCENT TECHNOLOGY

[75] Inventors: Michael J. Glass, Centerville; Jana Coombs; Sharon L. Malmstrom, both of Salt Lake City; Linxian Wu, Sandy, all of Utah

[73] Assignee: Gull Laboratories, Salt Lake City, Utah

[21] Appl. No.: 613,805

[22] Filed: Mar. 5, 1996

[51] Int. Cl.$^6$ ................. C12Q 1/68; C07H 21/04; C07H 21/02
[52] U.S. Cl. ................. 435/6; 435/7.92; 536/24.3; 536/24.32; 536/25.32; 935/77; 935/78
[58] Field of Search ................. 435/6, 7.92; 536/24.3, 536/25.32, 24.32; 935/78

[56] References Cited

U.S. PATENT DOCUMENTS

| | | | |
|---|---|---|---|
| 4,965,188 | 10/1990 | Mullis et al. | 435/6 |
| 5,424,841 | 6/1995 | Van Gelder et al. | 356/417 |
| 5,453,355 | 9/1995 | Birkenmeyer et al. | 435/6 |
| 5,459,034 | 10/1995 | Tabaqchali et al. | 435/6 |

FOREIGN PATENT DOCUMENTS

| | | |
|---|---|---|
| 0 266 881 A2 | 5/1988 | European Pat. Off. |
| 0 382 433 A2 | 8/1990 | European Pat. Off. |
| 0 617 288 A2 | 9/1994 | European Pat. Off. |
| WO 91/00511 | 1/1991 | WIPO |
| WO 92/05185 | 4/1992 | WIPO |
| WO 93/21345 | 10/1993 | WIPO |
| WO 94/02640 | 2/1994 | WIPO |
| WO 94/06936 | 3/1994 | WIPO |

OTHER PUBLICATIONS

Iitia, Antti et al. "Simultaneous Detection of Two Cystic Fibrosis Alleles Using Dual-Label Time-Resolved Fluorometry,"Molecular and Cellular Probes, 1992, vol. 6, pp. 505–511. (whole document).

DeBiasio, R., Bright, G.R., Ernst, L.A., Waggoner, A.S., Taylor, D.L., *Five–Parameter Fluorescence Imaging: Wound Healing of Living Swiss 3T3 Cells*, J. Cell Biology, 1987; 105: 1613–1622.

Ried, T., Baldini, A., Rand, T.C., Ward, D.C., *Simultaneous Visualization of Seven Different DNA Probes by in situ Hybridization Using Combinatorial Fluorescence and Digital Imaging Microscopy*, Proc. Natl. Acad. Sci. USA, 1992; 89: 1388–1392.

Iovannisci, D.M., Winn–Deen, E.S., *Ligation Amplification and Fluorescence Detection of Mycobacterium tuberculosis DNA*, Molecular and Cellular Probes, 1993; 7:35–43.

Vlieger, A.M., Medenblik, A.M.J.C., VanGijswijk, P.M., Tanke, H.J., Van Der Ploeg, M., Gratama, J.W., Raap, A.K., *Quantitation of Polymerase Chain Reaction Products by Hybridization–Based Assays with Fluorescent, Colorimetric, or Chemiluminescent Detection*, Analytical Biochemistry, 1992; 205:1–7.

Gudibande, S.R., Kenten, J.H., Link, J., Friedman, K. Massey, R. J., *Rapid, Non–Separation Electrochemiluminescent DNA Hybridization Assays for PCR Products, Using 3'–Labelled Oligonucleotide Probes*, Molecular and Cellular Probes, 1992, 6:495–503.

(List continued on next page.)

*Primary Examiner*—W. Gary Jones
*Assistant Examiner*—Paul B. Tran
*Attorney, Agent, or Firm*—Workman, Nydegger & Seeley

[57] ABSTRACT

The present invention provides methods and apparatus for detecting and discriminating multiple analytes within a test sample which are rapid, accurate, and convenient enough for routine use in a clinical laboratory. In particular, the present invention provides methods and apparatus for permitting multiple PCR-amplified target nucleic acid sequence hybrids within a single sample, labeled with different fluorescent dyes, to be spectrally distinguished using the readout data directly from a fluorescence reader instrument.

19 Claims, 5 Drawing Sheets

OTHER PUBLICATIONS

Wu, L., McCarthy, B.J., Kadushin, J.M., Nuss, C.E., *A Simple and Economic Method for Directly Performing PCR on Washed Blood Cells or on Whole Blood*, Transgenica, 1994; 1(1): 1–5.

Wu, L., Chaar, O., Bradley, K., Kadushin, J., *HLA DR DNA Typing With a Microtiter Plate–Based Hybridization Assay*, Hum. Immun. 1993; 37: p. 141.

Bauer, H., Ting., Y., Greer, C., Chambers, J., Tashiro, C., Chimera, J., Reingold, A., Monos, M., JAMA 265:472–477(1991), *Genital Human Papillomavirus Infection in Female University Students and Determined by a PCT–Based Method.*

Nuijten, P., Van Asten, F., Gaastra, W., Van Der Zeijst, B., J. Biol. Chem. 265:17798–17804 (1990), *"Structural and Functional Analysis of Two Campylobacter jejuni Flagellin Genes".*

Stone, G., Oberst, R., Hays, M., McVey, S., Chengappa, M., J. Clin. Miocrobiol. 32: 1742–1749 (1994), *Detection of Salmonella Serovars from Clinical Samples by Enrichment Broth Cultivation–PCR Precedure.*

Galan, J., Ginocchio, C., Costeas, P., J. Bacterial, 174:4338–4348 (1992), *Molecular and Functional Characterization of the Salmonella Invasion Gene invA; Homology of InvA to Members of a New Protein Family.*

Sakai, T., Saskawa, C., Makiro, S., Yoshikawa, M., Infect. Immun. 54:395–402 (1986), *DNA Sequence and Product Analysis of the virF Locus Responsible for Congo Red Binding and Cell Invasion in Shigella flexneri 2a.*

Yavzori, M., Cohen, D., Wasserlauf, R., Ambar, R., Rechavi, G., Ashkenazi, S., Eur. J. Clin. Microbiol. Infect. Dis. 13:232–237 (1994), *Identification of Shigella Species in Stool Specimens by DNA Amplification of Different Loci of the Shigella Virulence Plasmid.*

Yi-Kun, L., Qin, H., Molodysky, E., Morris, B., J. Virol. Methods 44L77–78 (1994), *Simple Microwave and Thermal Cycler Boiling Methods for Preparation of Cervicovaginal Lavage Cell Samples Prior to PCR For Human Papillomavirus Detection.*

Ohhara, M., Kursou, Y., Esumi, M., Biotechniques 17:726–728 (1994), *Direct PCR of Whole Blood and Hair Shafts by Microwave Treatment.*

Singh, R.K., Tell, S.G., White, C.T., Hoffman, D., Chi, V.L. & Erickson, B.W. (1993), *A Scalable Systolic Multiprocessor System for Analysis of Biological Sequences.* Research on Integrated Systems: Proceeding of the 1993 Symposium, MIT Press, Cambridge, MA, 168–182.

Cebula, T., Payne, W., Feng, P. J. Clin. Microbiol. 33:248–250 (1995), *Simultaneous Identification of Strains of Escherichia coli Serotype O157:H7 and Their Shiga–Like Toxin Type of Mismatch Amplification Mutation Assay–Multiplex PCR.*

Nakajima, H., Inoue, M., Mori, T., Itoh, K., Arakawa, E., Watanabe, H., J. Clin Microbiol. 30:2484–2486 (1992), *Detection and Identification of Yersinia pseudotuberculosis and Pathogenic Yersinia enterocolitica by Improved Polymerase Chain Reaction Method.*

Wegmuller, B., Luthy, Jr. Candrian, U., Applied and Environmental Microbiology, 59:2161–2165 (1993), *Direct Polymerase Chain Reaction Detection of Camylobacter jejuni and Campylobacter coli in Raw Milk and Dairy Products.*

Chamberlain, J., Gibbs, R., Ranier, J., Caskey, C., *PCR Protocols: A Guide to Methods and Applications.* pp. 272–281.

METHODS FOR DETECTION AND DISCRIMINATION OF MULTIPLE ANALYTES USING FLUORESCENT TECHNOLOGY

BACKGROUND OF THE INVENTION

1. Technical Field

This invention relates to nucleic acid sequence based detection technology. In particular, the present invention relates to methods and apparatus permitting multiple analytes within a single sample to be labeled with multiple distinguishable fluorescent dyes which are then detected and discriminated in a process that is rapid, accurate, and convenient enough for routine clinical laboratory use.

2. Background Information

Accurate detection of biological analytes present in various types of test samples is useful for many purposes including clinical, experimental, and epidemiological analyses. Because the genetic information in all living organisms is carried largely in the nucleic acids, either double-stranded deoxyribonucleic acid (DNA) or ribonucleic acid (RNA), detection and discrimination of specific nucleic acid sequences permits the presence, or absence, of a particular analyte within a test sample to be determined.

The development of the polymerase chain reaction (PCR) process for amplifying one or more targeted nucleic acid sequences within a sample or mixture of nucleic acid(s) has greatly facilitated processes for detecting and discriminating specific nucleic acid sequences. See, e.g., U.S. Pat. No. 4,965,188, the disclosure of which is herein incorporated by reference. PCR amplification has proven useful in numerous clinical applications including the detection and/or diagnosis of infectious diseases and pathological genomic abnormalities as well as DNA polymorphisms that may not be associated with any pathological state. One problem with PCR is that the process for preparing sample materials for the amplification of nucleic acid sequences are generally difficult and tedious.

In addition, there are many circumstances where it would be useful to simultaneously detect and discriminate between multiple target nucleic acid sequences present or potentially present within a test sample. For example, an accurate diagnosis of an infectious disease may require determining which, if any, of numerous possible infectious agents are present in a clinical sample. Generally, the sample must be suitably prepared and then divided into multiple portions such that separate PCR amplification procedures may be performed with different primers, if available, for the different potential target nucleic acid sequences. Again, this process is very repetitive and laborious.

In view of the foregoing, it would be advantageous to provide methods and apparatus for improving the efficiency and decreasing the time required to prepare and amplify multiple target nucleic acid sequences within a test sample by permitting various types of sample material to be prepared for DNA amplification without laborious nucleic acid extraction and purification steps. It would also be advantageous to provide methods and apparatus for improving the efficiency and decreasing the time required to prepare and amplify multiple targeted nucleic acid sequences within a test sample by permitting multiple target nucleic acid sequences within the sample to be simultaneously and non-preferentially amplified.

A co-pending application entitled METHODS AND APPARATUS FOR PREPARING, AMPLIFYING, AND DISCRIMINATING MULTIPLE ANALYTES, Ser. No. 08/587,209, filed Jan. 16, 1996, and assigned to the common assignee, Gull Laboratories, Inc. of Salt Lake City, Utah, discloses methods and apparatus comprising both rapid sample processing means for rapidly preparing sample material of various types for amplification of nucleic acid sequences and multianalyte non-preferential amplifying process means for simultaneously and non-preferentially amplifying multiple target nucleic acid sequences, if present within the sample. The rapid sample processing means comprises unique nucleic acid extraction buffer formulations and the multianalyte non-preferential amplifying process means comprises appropriate primer oligonucleotides optimized to achieve substantially similar amplification efficiencies under the process conditions. The disclosure of co-pending application Ser. No. 08/587,209 is herein incorporated by reference.

Numerous methods for detecting and discriminating nucleic acid sequences using oligonucleotide probes, i.e., probes complementary to the PCR-amplified products, are known. Typically, a solid phase system is used. For example, either the PCR amplified products or the probes may be affixed directly onto a series of membranes. The non-affixed components, i.e., either the probes or the PCR products, respectively, are then added to the separate membranes under hybridization conditions. Either the probes or the PCR products are labeled with some type of label moiety so as to be detectable by spectroscopic, photochemical, biochemical, immunochemical, or chemical means. Examples of label moieties include fluorescent dyes, electron-dense reagents, enzymes capable of depositing insoluble reaction products or of being detected chromogenically, such as horseradish peroxidase or alkaline phosphatase, a radioactive label such as $^{32}P$, or biotin. Hybridization between the PCR products and probes will occur only if the components are sufficiently complementary to each other. After hybridization, a washing process removes any non-hybridized molecules so that detection of remaining labeled component indicates the presence of probe/target nucleic acid hybrids.

In addition to the classic dot-blot detection methods, solid-phase systems utilizing microtiter plates are also known. Various methods have been used to immobilize the desired component, either the probe or the PCR products, onto the microplate. In one approach, hydrophobic action passively adsorbs the component onto the microplate. Alternatively, the biotin/avidin interaction is utilized by, for example, incorporating biotin onto the component and passively absorbing avidin molecules onto the microplate such that the biotinylated components become bound to the avidin. The use of covalent linking chemistry has recently been shown to produce more consistent and efficient binding of oligonucleotide probes to microplate plastic surfaces. In this technology, the oligonucleotide probes are attached covalently to chemical linkers on the plastic surface via the 5'-end phosphate group, amine group, or other reactive moiety. This approach does appear to improve efficiency while simplifying the procedure.

In view of the foregoing, it will be further appreciated that a sample containing multiple PCR-amplified target nucleic acid sequences could be divided into multiple separate sample portions so that a detection process for each potentially present analyte could be separately performed on the different portions. In this circumstance, each probe specific for a single analyte could be labeled with the same label moiety because each detection process is performed on a separate sample portion. Thus, any of the known labelling systems could be used to separately detect the multiple analytes in the different portions. Such separate and repetitive processing, however, is very time-consuming and inefficient.

It will thus be appreciated that it would be a significant advantage to be able to simultaneously process multiple distinguishably labeled analytes within a single sample such that the multiple analytes can be rapidly, accurately, and conveniently detected and discriminated. As mentioned above, various types of labeling moieties are known. Existing labeling technologies include colorimetric, fluorescence, bioluminescence, chemiluminescence, chemifluorescence, electrochemiluminescence, and radioisotope systems. Although there are multiple colorimetric systems, the various color-producing reaction processes are not compatible with each other and, thus, cannot be performed simultaneously in the same sample. In addition, the colorimetric systems are not sensitive enough for many applications. Greater sensitivity is achieved with bioluminescence, chemiluminescence, chemifluorescence and electrochemiluminescence systems. These systems, however, also depend on specific reaction processes, e.g., enzymatic or other chemical reactions or electrochemical excitation, to produce the detectable product. Hence, although multiple different processes are available, these cannot be performed simultaneously in the same sample. Radioisotope systems are capable of producing multiple distinguishable labels in the same sample, however, the use of radioactive substances requires time consuming and costly monitoring, reporting, and environmental hazard control procedures. Thus, radioisotope systems are generally unsuitable for routine clinical laboratory use.

Fluorescence-based technology provides multiple potentially distinguishable label moieties. In particular, fluorescent dyes are known which have differing emission and excitation spectra. In theory, the different spectra should be readily distinguishable. In practice, however, this has proven difficult except under controlled experimental conditions using relatively complex instrumentation and analysis techniques. See, e.g., DeBiasio, R., Bright, G. R., Ernst, L. A., Waggoner, A. S., Taylor, D. L., *Five-Parameter Fluorescence Imaging: Wound Healing of Living Swiss 3T3 Cells*, J. Cell Biology, 1987; 105: 1613–1622, Ried, T., Baldini, A., Rand, T. C., Ward, D. C., *Simultaneous Visualization of Seven Different DNA Probes by In Situ Hybridization Using Combinatorial Fluorescence and Digital Imaging Microscopy*, Proc. Natl. Acad. Sci. USA, 1992; 89:1388–1392.

In general, analytes labeled with different fluorescent dyes are separated using known separation techniques before detection. For example, a research study directed to developing a ligation chain reaction ("LCR") process to demonstrate the presence of *M. tuberculosis* organisms is reported in Iovannisci, D. M., Winn-Deen, E. S., *Ligation Amplification and Fluorescence Detection of Mycobacterium tuberculosis DNA*, Molecular and Cellular Probes, 1993; 7:35–43. The LCR products were labeled with four different fluorescent dyes to follow the reaction and demonstrate amplification of the desired target DNA sequence. The multiply-labeled LCR products were separated by gel electrophoresis and then analyzed using proprietary software for a specific fluorescent DNA sequencer instrument. PCR products labeled with two different fluorescent dyes were also examined by separation and detection in a laser-based electrophoretic instrument for the detection and quantitation of fluorescently tagged nucleic acid sequences.

A recent report appearing on the Internet Web Page of Molecular Dynamics, Inc. describes the detection and discrimination of two differently colored fluorescent dyes used to label allele-specific primers for detecting a gene mutation associated with cystic fibrosis. See, "application_notes/ AP54.ht" at internet address: http://www.mdyn.com/, dated Jan. 25, 1996. The differently labeled PCR amplified products were not separated. Rather, the products were captured on microplate sample wells and scanned with a FluorImager 575 using available bandpass filters. A proprietary image analysis software product was used to correct for the overlapping spectra of the fluorescent dyes.

At present, there is no available technology permitting detection and discrimination of multiple distinguishable fluorescent dye-labeled PCR amplification products, i.e., nucleic acid sequence hybrids, within a single sample in a manner which can be rapidly, accurately, and conveniently performed using the read-out data directly from a filter-based fluorescence reader instrument. Thus, it would be a significant advancement in the art to provide methods and apparatus for the detection and discrimination of multiple different fluorescent dye-labeled nucleic acid sequence hybrid molecules within a single sample which can be performed on a routine basis within a clinical laboratory using read-out data directly from a filter-based fluorescence reader instrument.

SUMMARY OF THE INVENTION

It is a primary object of the present invention to provide methods and apparatus for improving the efficiency of detection and discrimination of multiple analytes within a test sample.

It is another object of the present invention to provide methods and apparatus for detecting and discriminating multiple analytes within a test sample which are rapid, accurate, and convenient enough for routine use in a clinical laboratory. In particular, it is an object to provide methods and apparatus for permitting multiple PCR-amplified target nucleic acid sequence hybrids within a single sample, labeled with different fluorescent dyes, to be spectrally distinguished using the read-out data directly from a fluorescence reader instrument.

These and other objects and advantages of the invention will be better understood by reference to the detailed description, or will be appreciated by the practice of the invention. To achieve the foregoing objects, and in accordance with the invention as embodied and broadly described herein, the methods of the present invention comprise multianalyte recognition process means for detecting and discriminating multiple fluorescent dye-labeled nucleic acid sequence hybrids within a single sample. The multianalyte recognition process means utilizes multiple spectrally distinguishable fluorescent dye-labeled oligonucleotides and uniquely adapted filters to produce read-out data from a filter-based fluorescence reader instrument that directly distinguishes the multiple analytes.

DETAILED DESCRIPTION OF THE PREFERRED EMBODIMENTS

Figure 1A:
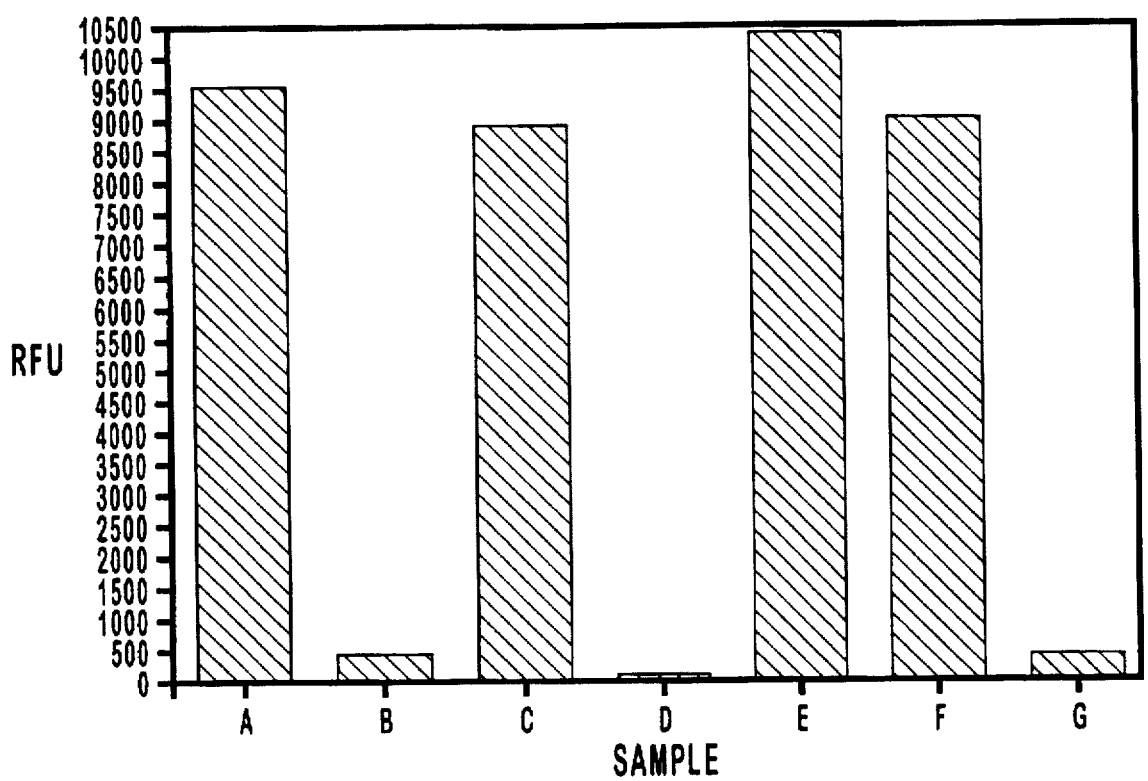
FIG. 1A is a graph illustrating fluorescence determinations in seven different samples assayed on a Bio-Tek FL500 Plate Reader using a filter set specific for Bodipy-labeled nucleic acid hybrids.

As reviewed in the background section, the development of the polymerase chain reaction (PCR) process for amplifying one or more targeted nucleic acid sequences within a sample or mixture of nucleic acid(s) has greatly facilitated processes for detecting and discriminating specific nucleic acid sequences. Routine use of PCR in clinical laboratories has been hampered by problems including the generally tedious process for preparing sample materials for the amplification of nucleic acid sequences and difficulties related to simultaneously amplifying multiple target nucleic acid sequences within a sample. A co-pending application entitled METHODS AND APPARATUS FOR PREPARING, AMPLIFYING, AND DISCRIMINATING MULTIPLE ANALYTES, Ser. No. 08/587,209, filed Jan. 16, 1996, incorporated herein by reference, and assigned to the common assignee, Gull Laboratories, Inc. of Salt Lake City, Utah, discloses methods and apparatus comprising both rapid sample processing means for rapidly preparing sample material of various types for amplification of nucleic acid sequences and multianalyte non-preferential amplifying process means for simultaneously and non-preferentially amplifying multiple target nucleic acid sequences, if present within the sample. The rapid sample processing means comprises unique nucleic acid extraction buffer formulations and the multianalyte non-preferential amplifying process means comprises appropriate primer oligonucleotides optimized to achieve substantially similar amplification efficiencies under the process conditions.

The present invention relates to the detection and discrimination of multiple analytes within a single sample following PCR amplification of multiple target nucleic acids. In particular, the present invention relates to methods and apparatus permitting multiple analytes within a single sample to be labeled with multiple distinguishable fluorescent dyes which are then detected and discriminated in a process that is rapid, accurate, and convenient enough for routine clinical laboratory use.

As reviewed in the background section, numerous methods for detecting and discriminating nucleic acid sequences using labeled oligonucleotide probes, i.e., probes complementary to the PCR-amplified products, are known. Existing labeling technologies include colorimetric, fluorescence, bioluminescence, chemiluminescence, chemifluorescence, electrochemiluminescence, and radioisotope systems. Thus, a sample containing multiple PCR-amplified target nucleic acid sequences could be divided into multiple separate sample portions so that a detection process for each potentially present analyte could be separately performed on the different portions. Such separate and repetitive processing, however, is time-consuming and inefficient.

Fluorescence-based technology provides multiple potentially distinguishable label moieties. Fluorochrome molecules emit fluorescent light upon returning to a lower energy state after being boosted to a higher energy, excited state due to the absorption of light energy. Each fluorochrome is excited by light of specific wavelengths and each fluorochrome emits light of specific wavelengths. Thus, different fluorochromes have different light absorption and emission patterns which are known as spectra. Because the excited state represents a higher energy state, the emission spectrum is always shifted toward lower energy, i.e., longer wavelengths, compared to the absorption spectrum. With the use of optical filters, this energy shift makes it possible to separate the excitation light and the emission light so that the emitted light can be detected with a scanning instrument. Optical filters are also generally required to minimize interfering background fluorescence.

Commercially available fluorescent dyes are known which have differing emission and excitation spectra. In theory, the different spectra should be readily distinguishable. In practice, however, this has proven difficult except under controlled experimental conditions using relatively complex instrumentation and analysis techniques. In general, analytes labeled with different fluorescent dyes are separated using known separation techniques before detection. It is also known to scan multiple fluorescent dyes and to use image analysis computer software to correct for the overlapping spectra of the fluorescent dyes.

Numerous studies have shown that environmental conditions and covalent linking of fluorescent dyes to macromolecules can effect the position and intensity of the spectra. Thus, the specific environment must be considered when selecting and evaluating a fluorescence-based detection system. At present, there is no available technology permitting detection and discrimination of multiple distinguishable fluorescent dye-labeled PCR amplification products, i.e., nucleic acid sequence hybrids, within a single sample in a manner which can be rapidly, accurately, and conveniently performed using the read-out data directly from a filter-based fluorescence reader instrument. The present invention is directed towards such a technology.

The methods and apparatus of the present invention are extremely versatile and are applicable to a wide range of uses. For example, simultaneous detection of and discrimination between multiple potentially present microorganisms in biological samples permits rapid diagnosis of infections. It would also be useful to rapidly detect and discriminate between multiple potentially present microorganisms in other types of samples, such as foodstuffs, for various purposes such as diagnostic/forensic or quality control purposes. Applications in genetic research are also numerous and versatile. The detection and discrimination of specific genetic sequences for purposes including diagnosing genetic disorders or identifying genetic variances, are rapidly, simply, and accurately performed in accord with the present invention.

The methods and apparatus of the present invention will be described both generally and with reference to a specific clinical application. One exemplary clinical application of the methods and apparatus of the present invention is the detection and discrimination among multiple potential infectious pathogens. In particular, the advantageous application of the methods and apparatus of the present invention will be described with reference to a Gastroenteritis Panel for assisting in diagnosing the cause of acute infectious bacterial gastroenteritis through stool sample analysis. The Gastroenteritis Panel is described in detail in co-pending Ser. No. 08/587,209, filed Jan. 16, 1996, and assigned to the common assignee, Gull Laboratories, Inc. of Salt Lake City, Utah.

There can be many causes of acute gastroenteritis. It is often important to differentiate acute gastroenteritis from other conditions which may present similar signs and symptoms. In addition, it can be critical in some cases of infectious etiology to determine the specific causative agent. In some circumstances, rapid initiation of specific and effective pharmacologic therapy may be life-saving while, in other circumstances, use of inappropriate antimicrobial agents can actually be detrimental to the patient. Five groups of potential infectious etiological agents for which a rapid detection and discrimination analysis would be particularly helpful are Salmonella species, Shigella species and enteroinvasive *Escherichia coli*, Campylobacter species, enterohemorrhagic *E. coli* (particularly *E. coli* O157:H7), and *Yersinia enterocolitica*.

The multianalyte nucleic acid sequence amplifying process disclosed in co-pending application Ser. No. 08/587, 209 permits non-preferential amplification of multiple analytes within a sample to proceed simultaneously. The multianalyte non-preferential amplifying process means employs unique primer oligonucleotides optimized to ensure that cross-reactivity is avoided and that amplification efficiency is substantially equal at the selected process conditions. For the gastroenteritis panel application, there are preferably six potential target nucleic acid sequences. Five are the potential pathogens, Salmonella, Shigella, *E. coli*, Campylobacter, and Yersinia microorganisms. A sixth is a control gene, β-globin, which should be present in every properly prepared sample. Optimized primer oligonucleotides were synthesized. Internal probe oligonucleotides, complementary to one strand of the amplification products of the PCR reactions performed with the optimized primers, were also obtained.

In the following examples, the present invention is illustrated with respect to detection and discrimination of multiple nucleic acid sequence hybrids derived from the target nucleic acid sequences useful for the gastroenteritis panel application. Selected characteristics of these sequences are presented in Table 1.

TABLE 1

SELECTED OLIGONUCLEOTIDE CHARACTERISTICS

| SEQ ID NO: | Oligonucleotide Designation | Modification | Gene | Map Position |
|---|---|---|---|---|
| 1 | SAL P.1 | 5'Amine | Salmonella invA gene[1] | 190-209 |
| 2 | αSAL P.1 | 5'Bodipy | | |
| 3 | SHIG P2.1 | 5'Amine | Shigella virF plasmid[2] | 675-696 |
| 4 | αSHIG-P2.1 | 5'Cy5 | | |
| 5 | CAMP P.1 | 5'Amine | Campylobacter flagellin gene[3] | 1929-1950 |
| 6 | αCAMP P.1 | 5'Tamera | | |
| 7 | YE 1.1 | 5'TET | Yersinia ail gene[4] | 547-566 |
| 8 | ECOP2 | 5'Texas Red | *Escherichia coli* uidA gene[5] | 383-400 |
| 9 | β-glob 1 | 5'Aminocoumarin | human βglobin gene[6] | 54-73 |

[1]Stone, G., Oberst, R., Hays, M, McVey, S., Chengappa, M., Detection of Salmonella Serovars from Clinical Samples by Enrichment Broth Cultivation-PCR Procedure, J. Clin. Microbiol.; 32: 1742–1749 (1994).
[2]Yavzori, M., Cohen, D., Wasserlauf, R., Ambar, R., Rechavi, G., Ashkenazi, S., Identification of Shigella Species in Stool Specimens by DNA Amplification of Different Loci of the Shigella Virulence Plasmid, Eur. J. Clin. Microbiol. Infect. Dis.; 13: 232–237 (1994).

TABLE 1-continued

SELECTED OLIGONUCLEOTIDE CHARACTERISTICS

| SEQ ID NO: | Oligonucleotide Designation | Modification | Gene | Map Position |
|---|---|---|---|---|

[3]Wegmuller, B., Luthy, J., Candrian, U., Direct Polymerase Chain Reaction Detection of *Campylobacter jejuni* and *Campylobacter coli* in Raw Milk and Dairy Products, Applied and Environmental Microbiology; 59: 2161–2165 (1993).
[4]Nakajima, H., Inoue, M., Mori, T., Itoh, K., Arakawa, E., Watanabe, H., Detection and Identification of *Yersinia pseudotuberculosis* and Pathogenic *Yersinia enterocolitica* by Improved Polymerase Chain Reaction Method, J. Clin. Microbiol.; 30: 2484–2486 (1992).
[5]Cebula, T., Payne, W., Feng, P., Simultaneous Identification of Strains of *Escherichia coli* Serotype O157:H7 and Their Shiga-Like Toxin Type by Mismatch Amplification Mutation Assay-Multiplex PCR, J. Clin. Microbiol.; 33: 248–250 (1995).
[6]Bauer, H., Ting, Y., Greer, C., Chambers, J., Tashiro, C., Chimera, J., Reingold, A., Monos, M., Genital Human Papillomavirus Infection in Female University Students and Determined by a PCR-Based Method, JAMA; 265: 472–477 (1991).

EXAMPLE 1

MATERIALS AND METHODS

I. COVALENT ATTACHMENT OF NUCLEIC ACID PROBES

Nucleic acid probes, SEQ ID NOS: 1, 3, and 5, were synthesized by Genosys Biotechnologies, Inc (The Woodlands, Tex., USA). The sequence of each probe is shown in Table 2. The probes were synthesized with a 5'terminal primary amine. N-oxysuccinimide amine binding microtiter plates (Corning Costar Corporation, Cambridge, Mass., USA) were used as the solid phase attachment support for the nucleic acid probes. Each probe was diluted to 10 micrograms/milliliter (µg/ml) in phosphate buffered saline (PBS), pH 7.25, and 100 µl of each probe was placed in each test well. The plate was incubated overnight at room temperature. After incubation, the solution was aspirated and the plate washed 5 times with 300 µl wash buffer/well (2.0 mM Imidazole buffered saline, 0.02% Tween-20)(all chemicals obtained from Sigma Chemical Co., St. Louis, Mo., USA). The remaining active sites were blocked with Stabilcoat (BSI Corporation, Eden Prairie, Minn., USA) for 30 minutes at room temperature. The wells were aspirated and used directly for hybridization.

TABLE 2

PROBE SEQUENCES

| SEQ ID NO: | DESIGNATION | SEQUENCE |
|---|---|---|
| 1 | SAL P.1 | 5'-TGG TTG ATT TCC TGA TCG C-3' |
| 3 | SHIG P2.1 | 5'-CTG ATC AGA TAA GGA AGA TTG-3' |
| 5 | CAMP P.1 | 5'-AAA CTT GGA ACA CTT CTT GCT-3' |

II. DNA HYBRIDIZATION/FLUORESCENT DETECTION

Anti-probes, designed to be exact DNA complements of the nucleic acid probes and labeled with different fluorescent dyes at the 5'terminus, SEQ ID NOS: 2, 4, and 6, were synthesized by Genemed Biotechnologies (San Francisco, Calif.). The DNA sequence and attached fluorescent dyes are shown in Table 3.

TABLE 3

ANTI-PROBE SEQUENCES AND ATTACHED FLUORESCENT DYES

| SEQ ID NO: | DESIGNATION | DYE | SEQUENCE |
|---|---|---|---|
| 2 | αSAL P.1 | Bodipy[1] | 5'-G CGA TCA GGA AAT CAA CCA-3' |
| 4 | αSHIG P2.1 | Cy5[2] | 5'-CAA TCT TCC TTA TCT GAT CAG-3' |
| 6 | αCAMP P.1 | Tamera[1] | 5'-AGC AAG AAG TGT TCC AAG TTT-3' |

[1]Proprietary product of Molecular Probes, Inc., Eugene, OR.
[2]Proprietary product of Amersham Life Science, Arlington Heights, IL.

Equal concentrations of each of the single-stranded oligonucleotides (approximately $1 \times 10^{14}$ molecule) were diluted in 50 μl of PBS, pH 7.25, and added with denaturing solution (final concentration, 0.4N NaOH) to each probe-coated well such that some wells contained only one anti-probe, some contained two anti-probes, and some contained all three anti-probes. Blank wells were also used as controls. Accordingly, there are seven different hybridization mixtures as follows:

| Sample Designation | Hybridization Mixture |
|---|---|
| A | Three probes plus three labeled anti-probes |
| B | Three probes plus Tamera-labeled αCAMP P.1 anti-probe only |
| C | Three probes plus Bodipy-labeled αSAL P.1 anti-probe only |
| D | Three probes plus Cy5-labeled αSHIG-P2.1 anti-probe only |
| E | Three probes plus dye-labeled αCAMP P.1 and αSAL P.1 anti-probes |
| F | Three probes plus dye-labeled αSAL P.1 and αSHIG-P2.1 anti-probes |
| G | Three labeled anti-probes plus CAMP P.1 and SHIG P2.1 probes |

Although the initial oligonucleotides were single-stranded, the denaturing and renaturing procedure was used to ensure compatibility with this method and double-stranded DNA molecules. After incubation for 10 minutes at room temperature, hybridization solution (final concentration, PBS, pH 7.25, 2% BSA) and neutralizing solution (final concentration, 1M ammonium acetate, pH 5.5) were added and incubated for a further 5 minutes at room temperature. The plate was then incubated for 1 hour at 55° C. Following incubation, the plate was washed 5 times with wash buffer (1M Tris buffered saline, pH 7.5, 1.0% Tween 20) at room temperature.

For fluorescence detection, 100 μl of PBS, pH 7.4, was added to each well and the plate was read directly on the FL500 Microplate Fluorescence Reader (Bio-Tek Instruments, Inc., Laguna Hills, Calif.). The filter combination (center wavelength in nanometers/bandwidth in nanometers) and sensitivity settings for each dye were as follows: Bodipy, excitation 485/20, emission 530/25, sensitivity 60; Cy5, excitation 590/20, emission 645/40, sensitivity 80; Tamera, excitation 530/25, emission 590/35, sensitivity 60. The data was recorded as relative fluorescent units ("RFU").

RESULTS

Figure 1B:
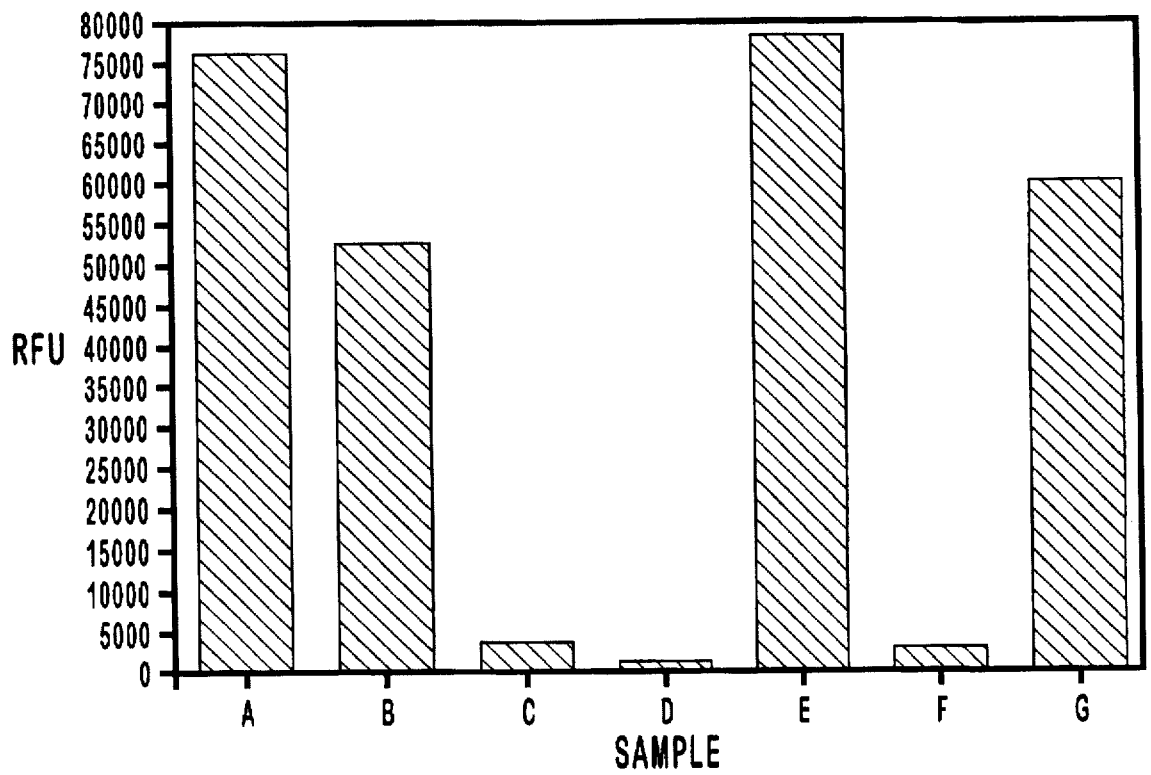
FIG. 1B is a graph illustrating fluorescence determinations in seven different samples assayed on a Bio-Tek FL500 Plate Reader using a filter set specific for Tamera-labeled nucleic acid hybrids.
Figure 1C:
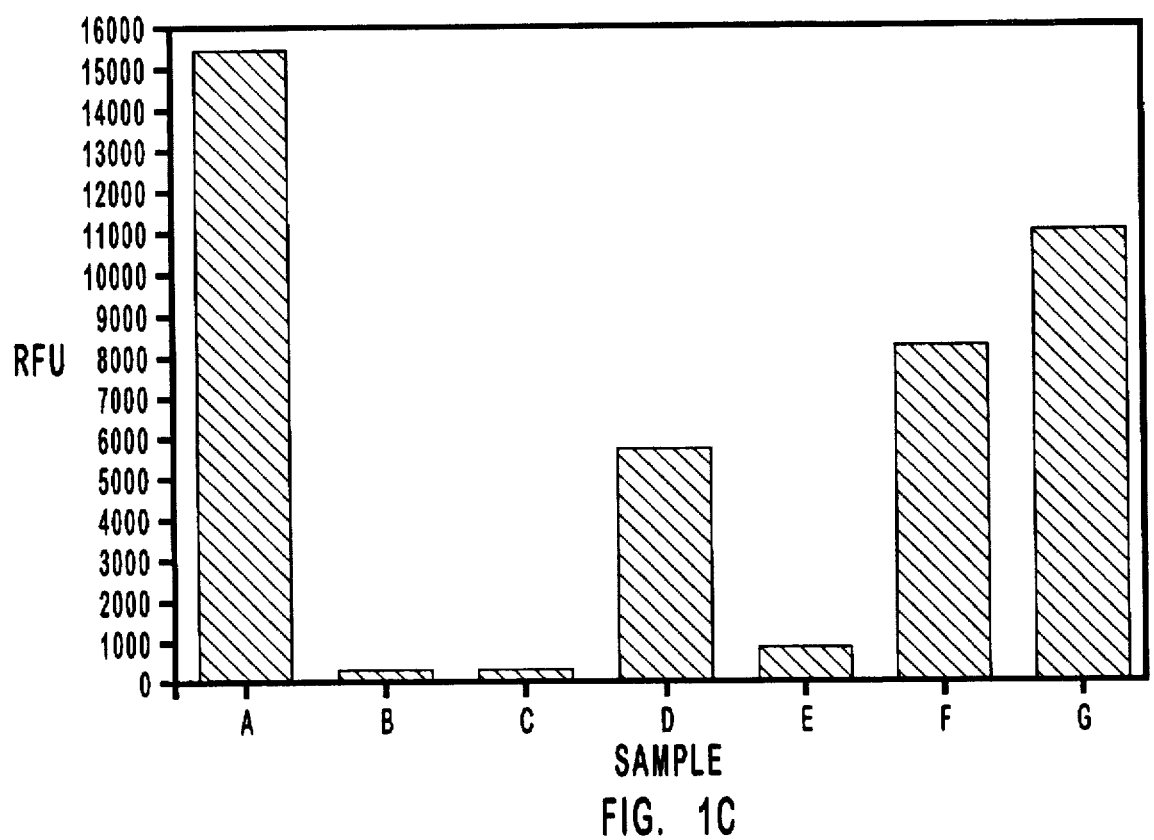
FIG. 1C is a graph illustrating fluorescence determinations in seven different samples assayed on a Bio-Tek FL500 Plate Reader using a filter set specific for Cy5-labeled nucleic acid hybrids.
Figure 2A:
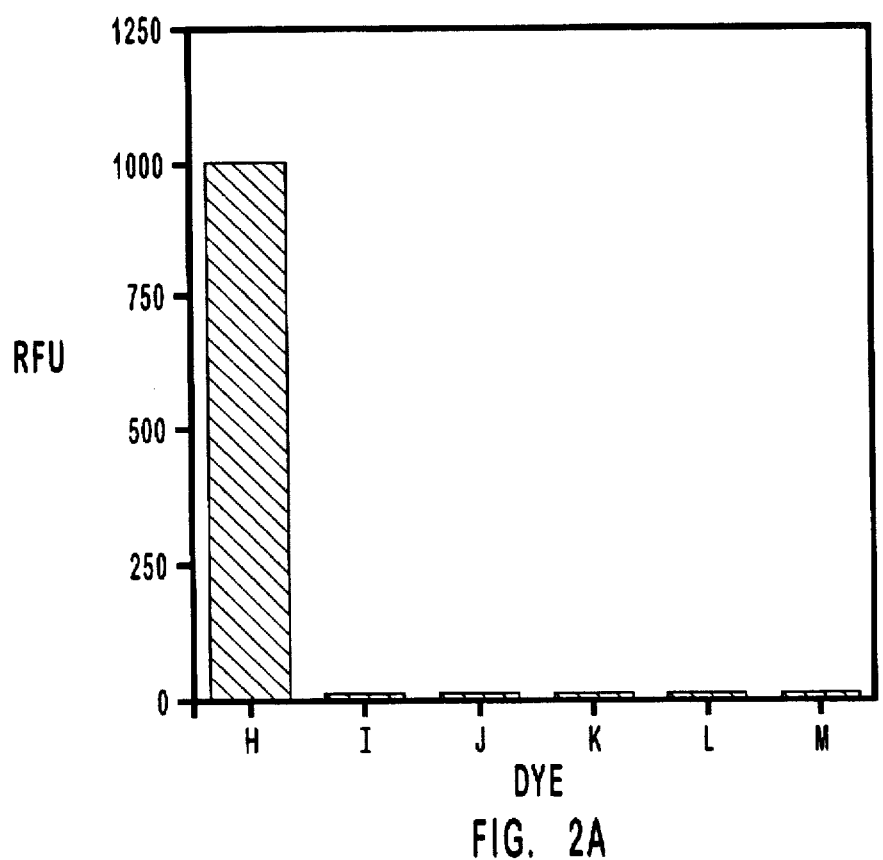
FIG. 2A is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for Aminocoumarin dye.
Figure 2B:
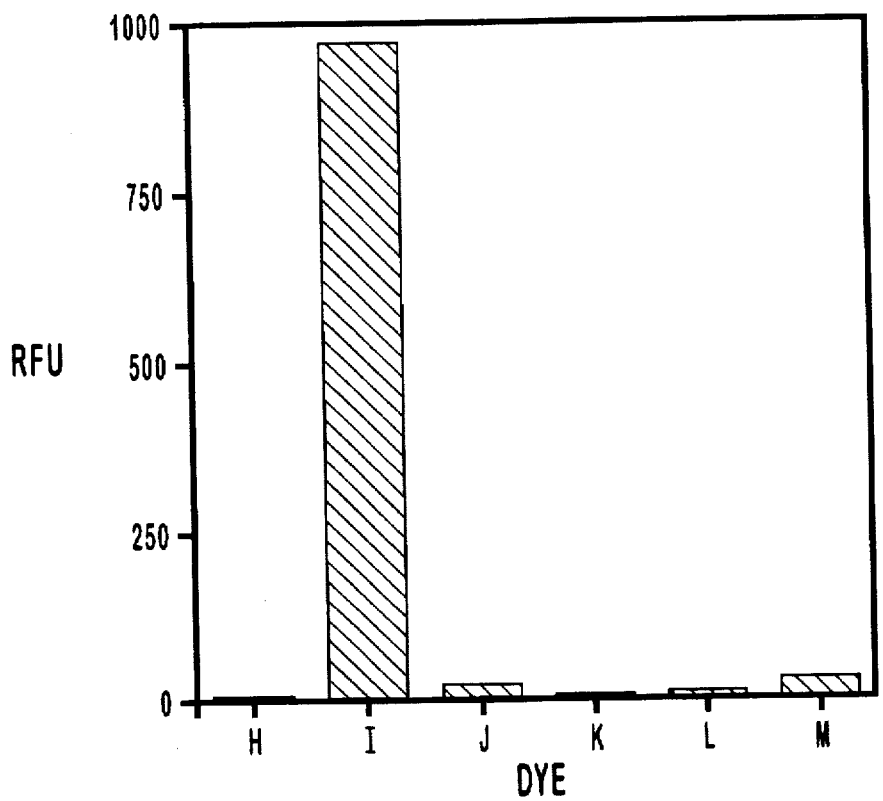
FIG. 2B is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for Bodipy dye.
Figure 2C:
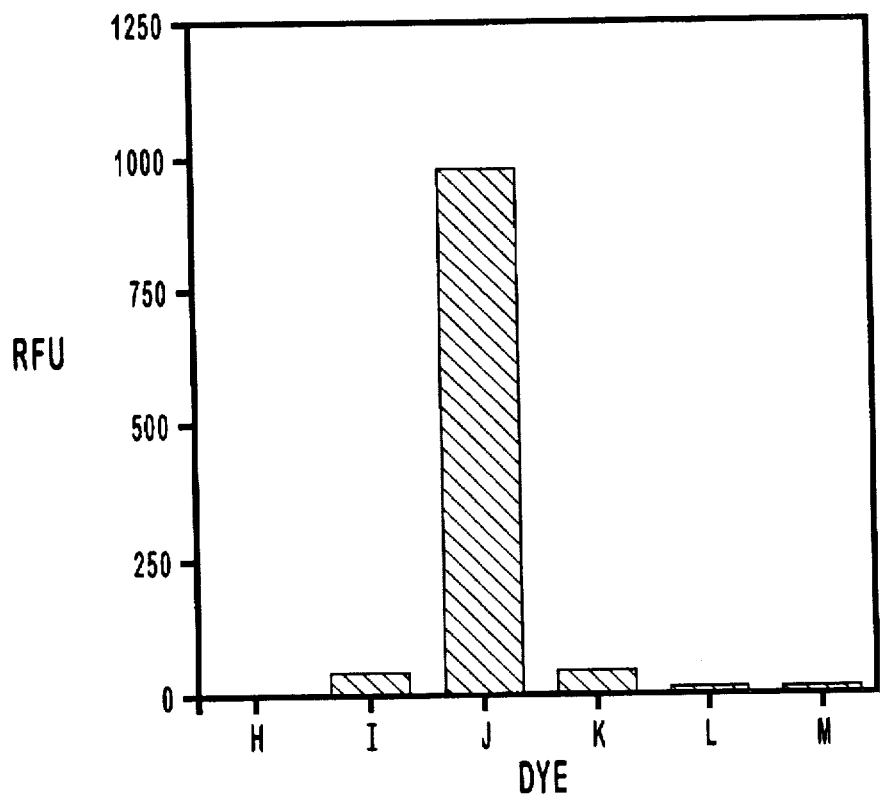
FIG. 2C is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for TET dye.
Figure 2D:
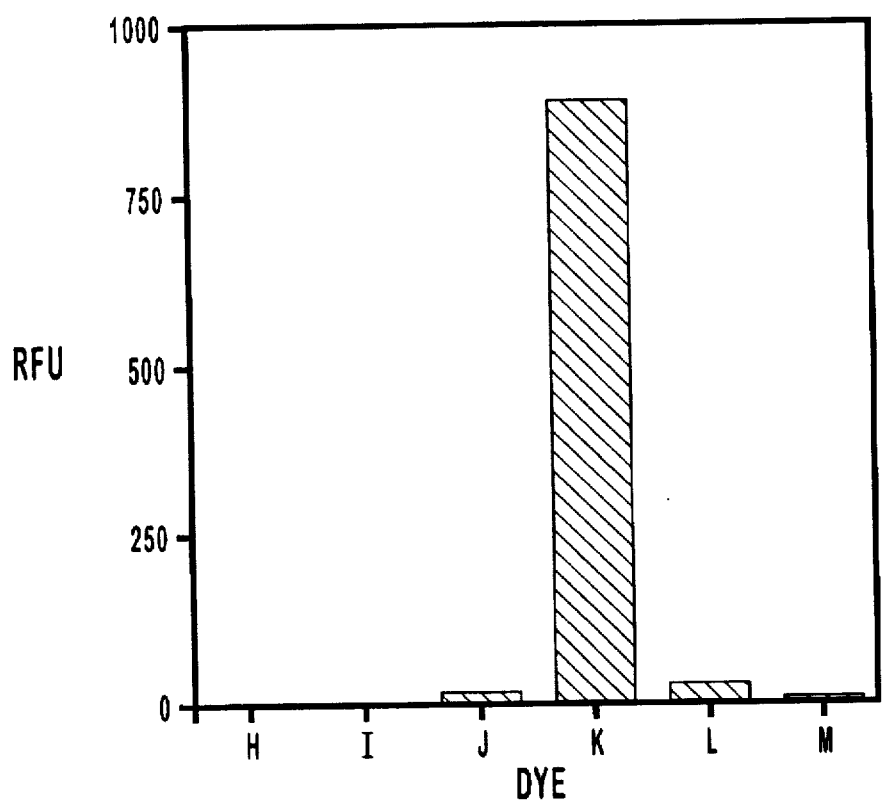
FIG. 2D is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for Tamera dye.
Figure 2E:
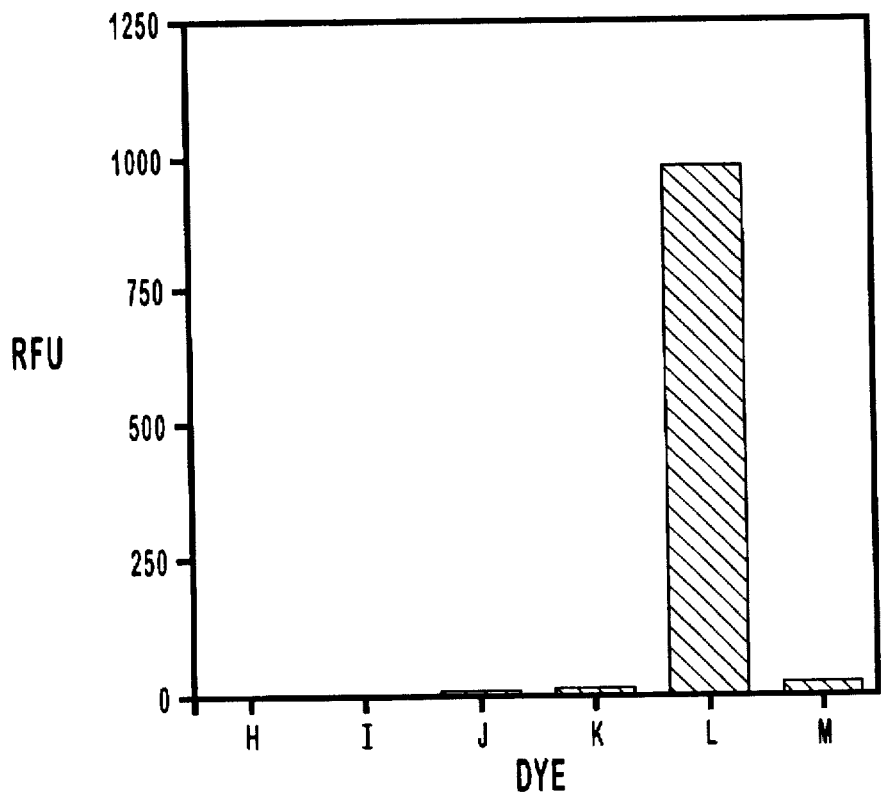
FIG. 2E is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for Texas Red dye.
Figure 2F:
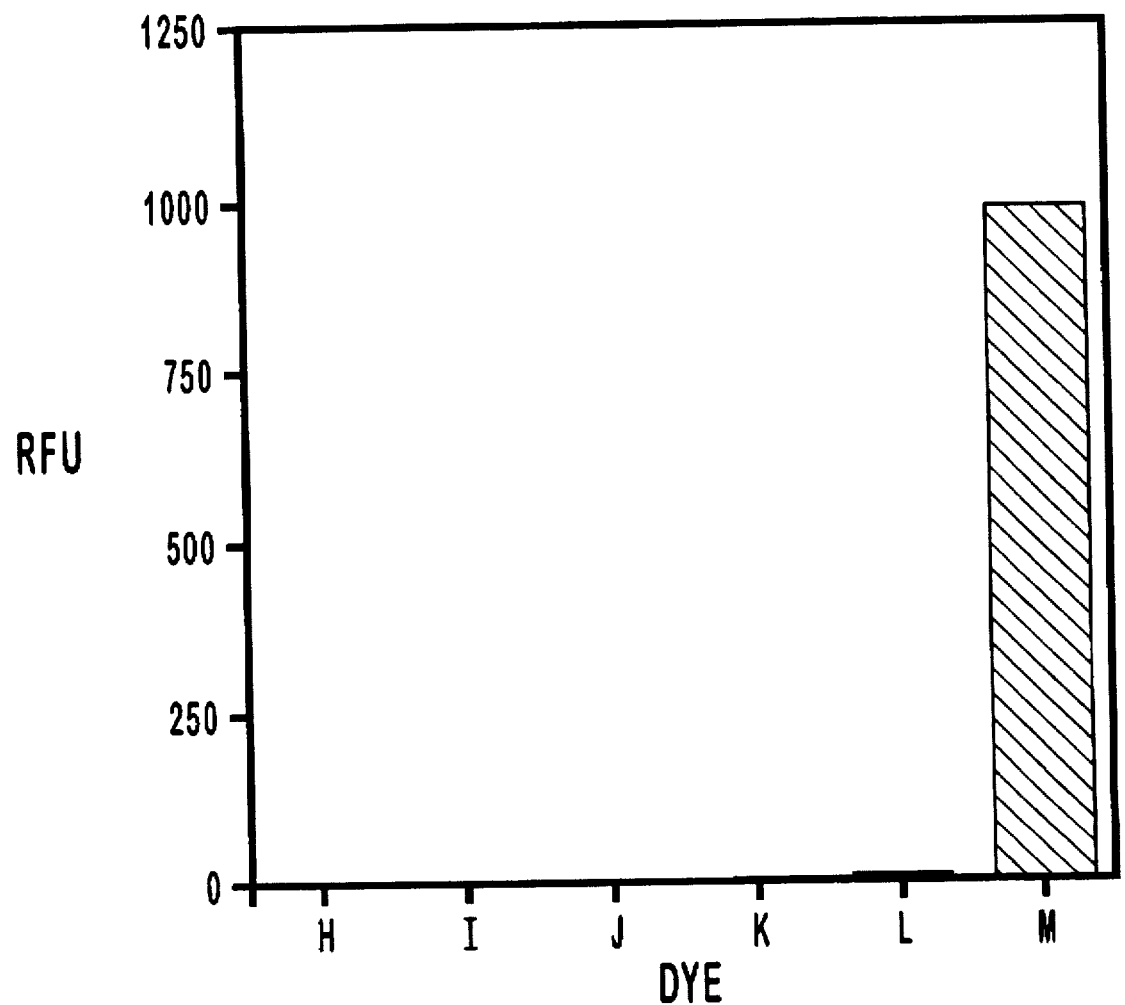
FIG. 2F is a graph illustrating the fluorescent signal from six different dye-labeled oligonucleotides when solutions containing the dye-labeled oligonucleotides were assayed on the Perkin Elmer LS-50 Luminescence Spectrometer at monochromator settings selected for Cy5 dye.

The anti-probe system is a well-controlled method for hybridization studies which illustrates principles used in DNA-DNA hybridization systems. The data obtained is useful for determining hybridization parameters applicable to a variety of systems. FIGS. 1A–1C show the results from a typical experiment using the labeled anti-probes, αCAMP P.1, αSAL P.1, and αSHIG P2.1, as analytes in the multiple recognition system. The three graphs illustrate fluorescence determinations in the seven different sample types assayed on a microplate reader instrument using filter sets specific for the Bodipy, Tamera, and Cy5 fluorescent dyes covalently linked to the three different anti-probes. The filter sets were predetermined by the manufacturer of the specific fluorometer instrument (Bio-Tek Instruments, Inc., Laguna Hills, Calif.). Sensitivity settings were analyzed to give the best sensitivities and signal-to-noise ratio. Therefore, the experimental design was constructed to match the existing commercially available filter sets.

The experiments were designed to identify the contribution of each individual dye within the mixture of the three dyes to the total fluorescence. FIG. 1 shows the results from a typical experiment. FIG. 1A shows the results using the Bodipy filter set. FIG. 1A demonstrates that the fluorescence in the mixture was due specifically to the excitation of the Bodipy-labeled αSAL P.1 anti-probe molecules hybridized to the SAL P.1 probes. The samples that contained these hybrids, i.e., Samples A, C, E, and F, gave a fluorescent signal greater than the cut-off which was determined to be 10 standard deviations above the signal from the blank samples. The other dyes in the mixtures did not exhibit a signal that was above the cut-off. Therefore, any combination of the other dyes in the mixture, i.e., Samples B, D, and G, did not contribute to the positive signal. FIG. 1B shows the results using the Tamera filter set. Again, it is evident that the fluorescence in the mixtures was due specifically to the excitation of the Tamera-labeled αCAMP P.1 anti-probe molecules present in hybrids with the CAMP P.1 probes in Samples A, B, E, and G. FIG. 1C similarly demonstrates that, using the Cy5 filter set, only the samples containing the hybridized Cy5-labeled αSHIG P2.1 anti-probes, i.e., Samples A, D, F, and G, gave signals above the cut-off.

This example demonstrates that three different analytes within a single sample can be labeled with selected fluorescent dyes and spectrally distinguished using read-out data directly from a filter-based fluorescence reader instrument with the use of selected filter sets and a solid phase hybridization system utilizing a microtiter plate format. Both time-consuming separation of the multiple analytes and the need for expensive and sophisticated instruments and data analysis procedures are avoided. Thus, the present invention could be advantageously utilized to rapidly, accurately, and conveniently detect and discriminate multiple nucleic acid sequence hybrids within a single sample on a routine basis in a clinical laboratory.

EXAMPLE 2

Filter configurations of commercially available fluorescent microtiter plate readers are not designed to spectrally distinguish multiple dyes from each other. Thus, it was found to be possible to discriminate only three different fluorescent dye-labeled analytes using available filter sets. Nevertheless, it has been discovered that custom designing of filter sets would allow for discrimination of additional dyes.

Six dyes were chosen for analysis on the basis of published excitation and emission spectra. Extensive literature reviews of fluorescent dye excitation and emission spectra indicated that these six dyes have minimal overlapping spectra. The six dyes, covalently linked to DNA oligonucleotides as described in Table 1, were purchased from three commercial suppliers. Three of the dyes, covalently linked to anti-probes as shown in Table 3, were used in the experiments described in Example 1. All six of the oligonucleotide sequences and the dyes attached at the 5'terminus, SEQ ID NOS: 2, 4, 6, 7, 8, and 9, are shown in Table 4. All of the oligonucleotides, except the YE 1.1 oligonucleotide (SEQ ID NO: 7), were obtained from Genemed Biotechnologies (San Francisco, Calif.). The YE 1.1 oligonucleotide was obtained from Keystone Laboratories, Inc. (Menlo Park, Calif.).

TABLE 4

OLIGONUCLEOTIDE SEQUENCES AND ATTACHED FLUORESCENT DYES

| SEQ ID NO: | DESIGNATION | DYE | SEQUENCE |
| --- | --- | --- | --- |
| 2 | αSAL P.1 | Bodipy[1] | 5'-G CGA TCA GGA AAT CAA CCA-3' |
| 4 | αSHIG P2.1 | Cy5[2] | 5'-CAA TCT TCC TTA TCT GAT CAG-3' |
| 6 | αCAMP P.1 | Tamera[1] | 5'-AGC AAG AAG TGT TCC AAG TTT-3' |
| 7 | YE 1.1 | TET[3] | 5'-TGT GTA CGC TGC GAG TGA AA-3' |
| 8 | ECO P2 | Texas Red[1] | 5'-TGG AAT TGA GCA GCG TTG-3' |
| 9 | β-glob 1 | Aminocoumarin[1] | 5'-CAA CTT CAT CCA CGT TCA CC-3' |

[1]Proprietary product of Molecular Probes, Inc., Eugene, OR.
[2]Proprietary product of Amersham Life Science, Arlington Heights, IL.
[3]Proprietary product of Perkin Elmer, Foster City, CA.

Numerous studies have shown that environmental conditions and covalent linking of fluorescent dyes to macromolecules can effect the position and intensity of the spectra. Thus, it was necessary to develop specific excitation and emission spectra for the six labeled oligonucleotides under conditions suitable for performance of DNA-DNA hybridization assays utilizing microtiter plate solid phase systems. Each individual dye was added to PBS, pH 7.4, to yield a concentration of ~$10^{14}$ molecules/ml. Each dye solution was then assayed in a quartz cuvette on a Perkin Elmer LS-50 Luminescence Spectrometer (Norwalk, Conn.) and dye-specific excitation and emission spectra (data not shown) were developed. This information was processed to determine a range of each spectra that would permit specific detection of each dye.

To verify these determinations, monochromator settings were derived and tested for each dye. It was determined that the available filter combination having the excitation setting of 360/40 and emission setting of 460/40 on the FL500 Microplate Fluorescence Reader (Bio-Tek Instruments, Inc., Laguna Hills, Calif.) was sufficient to distinguish aminocoumarin-labeled oligonucleotides from the other labeled oligonucleotides used in these experiments. Thus, a custom-designed filter combination derived from optimal monochromator setting determinations was not required for this dye.

A series of monochromator settings was tested for each of the other dyes to determine optimal settings for distinguishing between the six dyes. Solutions of the six dye-labeled oligonucleotides were assayed in the LS-50 Spectrometer at various monochromator settings and the signal intensity was measured. A maximum intensity was considered to be 1000 RFU. The data for the oligonucleotides labeled with bodipy, TET, Tamera, Texas Red, and Cy5 are presented in Tables 5–9, respectively.

TABLE 5

BODIPY-Labeled Oligonucleotides

| Monochromator Settings: Excitation Emission | Signal | Monochromator Settings: Excitation Emission | Signal |
| --- | --- | --- | --- |
| 485/2.5 507/5 | 154.2 | 520/2.5 540/5 | 60.87 |
| 485/5 507/5 | 132.5 | 520/5 540/5 | 53.02 |
| 485/5 507/10 | 639 | 520/5 540/8 | 207.5 |
| 485/2.5 | 224.9 | 520/5 | 341 |

TABLE 5-continued

BODIPY-Labeled Oligonucleotides

| Monochromator Settings: Excitation Emission | Signal | Monochromator Settings: Excitation Emission | Signal |
| --- | --- | --- | --- |
| 510/5 | | 540/10 | |
| 485/2.5 510/10 | 966.9 | 520/2.5 545/10 | 302 |
| 485/5 510/5 | 188.5 | 525/5 540/5 | 34.27 |
| 485/5 510/10 | 828 | 525/5 545/5 | 16.2 |
| 485/10 510/5 | 172.4 | 525/5 550/5 | 13.46 |
| 485/2.5 515/5 | 307.8 | 555/5 570/6 | 1.532 |
| 485/2.5 515/10 | 1000 | 600/5 620/10 | 0.68 |
| | | 640/10 680/20 | 0.259 |

TABLE 6

TET-Labeled Oligonucleotides

| Monochromator Settings: Excitation Emission | Signal | Monochromator Settings: Excitation Emission | Signal |
| --- | --- | --- | --- |
| 485/2.5 510/5 | 73.95 | 525/5 540/5 | 1000 |
| 485/2.5 510/10 | 13.3 | 525/5 540/8 | 1000 |
| 485/5 | 11.18 | 525/5 | 623.4 |

TABLE 6-continued

TET-Labeled Oligonucleotides

| Monochromator Settings: Excitation Emission | Signal | Monochromator Settings: Excitation Emission | Signal |
|---|---|---|---|
| 510/5 | | 545/5 | |
| 485/5 | 64.68 | 525/5 | 494.3 |
| 510/10 | | 550/5 | |
| 485/10 | 9.44 | 545/10 | 13.47 |
| 510/5 | | 575/5 | |
| 485/2.5 | 190.7 | 555/5 | 13.31 |
| 515/10 | | 570/6 | |
| 520/5 | 780 | 555/10 | 8.959 |
| 540/5 | | 570/6 | |
| 520/5 | 1000 | 600/5 | 1.018 |
| 540/10 | | 620/10 | |
| | | 640/10 | 0.22 |
| | | 665/10 | |

TABLE 7

TAMERA-Labeled Oligonucleotides

| Monochromator Settings: Excitation Emission | Signal | Monochromator Settings: Excitation Emission | Signal |
|---|---|---|---|
| 485/2.5 | 7.911 | 555/10 | 831.1 |
| 510/10 | | 570/7 | |
| 525/5 | 4.5 | 555/10 | 434.9 |
| 540/5 | | 575/5 | |
| 525/5 | 25.99 | 555/5 | 490.5 |
| 540/10 | | 580/5 | |
| 525/10 | 87.98 | 555/5 | 1000 |
| 540/10 | | 585/5 | |
| 545/10 | 299.2 | 555/5 | 446.3 |
| 575/5 | | 585/10 | |
| 550/5 | 415.2 | 555/5 | 1000 |
| 580/5 | | 590/5 | |
| 555/5 | 314.1 | 590/5 | 382 |
| 565/5 | | 610/10 | |
| 555/10 | 383.9 | 590/10 | 111.6 |
| 570/5 | | 610/10 | |
| 555/5 | 888.6 | 595/5 | 104.3 |
| 570/6 | | 615/10 | |
| 555/10 | 588 | 600/5 | 58.95 |
| 570/6 | | 620/10 | |
| | | 640/10 | 12.48 |
| | | 680/20 | |

TABLE 8

Texas Red-Labeled Oligonucleotides

| Monochromator Settings: Excitation Emission | Signal | Monochromator Settings: Excitation Emission | Signal |
|---|---|---|---|
| 485/2.5 | 10.44 | 555/5 | 79.89 |
| 510/10 | | 580/5 | |
| 525/5 | 3.357 | 555/5 | 378.6 |
| 540/5 | | 580/10 | |
| 545/5 | 211.9 | 590/5 | 1000 |
| 575/10 | | 610/10 | |
| 545/5 | 43.76 | 590/10 | 1000 |
| 575/5 | | 610/10 | |
| 545/10 | 40.18 | 595/5 | 214.5 |
| 575/5 | | 625/5 | |
| 555/5 | 28.66 | 595/10 | 198.7 |
| 570/6 | | 625/5 | |

TABLE 8-continued

Texas Red-Labeled Oligonucleotides

| Monochromator Settings: Excitation Emission | Signal | Monochromator Settings: Excitation Emission | Signal |
|---|---|---|---|
| 555/10 | 47.25 | 600/5 | 292.3 |
| 570/6 | | 620/5 | |
| 555/10 | 90.36 | 600/5 | 1000 |
| 570/7 | | 620/10 | |
| 555/5 | 264.3 | 600/5 | 1000 |
| 575/10 | | 625/10 | |
| 555/10 | 51.79 | 600/5 | 167.9 |
| 575/5 | | 630/5 | |
| 555/10 | 80.73 | 600/5 | 831.7 |
| 575/6 | | 630/10 | |
| 555/10 | 134.2 | 640/10 | 1.425 |
| 575/7.5 | | 680/20 | |
| 555/2.5 | 440.9 | | |
| 580/10 | | | |

TABLE 9

Cy5-Labeled Oligonucleotides

| Monochromator Settings: Excitation Emission | Signal | Monochromator Settings: Excitation Emission | Signal |
|---|---|---|---|
| 485/2.5 | 22.35 | 595/5 | 12.91 |
| 510/10 | | 615/10 | |
| 525/5 | 4.341 | 600/5 | 20.91 |
| 540/5 | | 620/10 | |
| 555/5 | 8.531 | 640/10 | 737.3 |
| 570/6 | | 670/10 | |
| 590/5 | 8.824 | 640/5 | 1000 |
| 610/10 | | 640/20 | |
| | | 640/10 | 1000 |
| | | 680/20 | |

The optimal monochromator settings were determined by analyzing the signal intensity of each specific dye-labeled oligonucleotide and the amount of cross-reactive signal seen with the other dye-labeled oligonucleotides. The selected optimal monochromator settings for each specific dye-labeled oligonucleotide were as follows:

| Dye | Excitation setting | Emission setting |
|---|---|---|
| Aminocoumarin | 360/40.0 | 460/40.0 |
| Bodipy | 485/2.5 | 510/10.0 |
| TET | 525/5.0 | 540/5.0 |
| Tamera | 555/5.0 | 570/6.0 |
| Texas Red | 600/5.0 | 620/10.0 |
| Cy5 | 640/10.0 | 680/20.0 |

FIGS. 2A–2F show graphs of the fluorescent signal of each dye-labeled oligonucleotide obtained when solutions containing the six dye-labeled oligonucleotides were assayed on the Perkin Elmer LS-50 Luminescence Spectrometer. The data was recorded as relative fluorescent units. The sample designations used in FIGS. 2A–2F are shown below:

| Sample Designation | Dye |
|---|---|
| H | Aminocoumarin |
| I | Bodipy |
| J | TET |
| K | Tamera |
| L | Texas Red |
| M | Cy5 |

As seen in FIGS. 2A–2F, in every case, the signal of the dye-labeled oligonucleotide specifically targeted with the optimal monochromator settings is greater than 10-fold the signal of the other dye-labeled oligonucleotides at that setting. It will be appreciated by those of skill in the art that these monochromator settings that give the best discrimination can be used to custom-design combination filters for the microplate fluorescent reader instrument which meet the derived specifications. In this manner, the six different dye-labeled oligonucleotides would be distinguishable on the basis of the direct read-out from the microplate fluorescence reader utilizing the appropriate combination filter.

It will be further appreciated by those of skill in the art that the methods and apparatus of the present invention are useful for permitting detection and discrimination of multiple distinguishable fluorescent dye-labeled PCR amplification products, i.e., nucleic acid sequence hybrids, within a single sample in a manner which can be rapidly, accurately, and conveniently performed using the read-out data directly from a filter-based fluorescence reader instrument.

The present invention may be embodied or utilized in other specific forms or manners without departing from its spirit or essential characteristics. The described embodiments and methods are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method for detecting and discriminating multiple target nucleic acid sequences, if present, within a mixture of multiple target nucleic acid sequences resulting from a selective polymerase chain reaction amplification process, said method comprising the steps of:
   obtaining a mixture of different fluorescent dye-labeled target nucleic acid sequences resulting from a selective polymerase chain reaction amplification process Using primer oligonucleotides labeled with multiple fluorescent dyes such that each different target nucleic acid sequence is labeled with a different fluorescent dye;
   obtaining multiple probe oligonucleotides, each said probe oligonucleotide being complementary to a portion of one strand of one target nucleic acid sequence such that said probe oligonucleotides can form hybrids with said fluorescent dye-labeled target nucleic acid sequences;
   obtaining a solid-phase system comprising a microtiter plate having microtiter wells and chemical linking means for efficiently binding said probe oligonucleotides to said microtiter wells;
   effecting chemical linking of said probe oligonucleotides to said microtiter wells to thereby immobilize said probe oligonucleotides in said microtiter wells:
   effecting hybridization of the probe oligonucleotides and the fluorescent dye-labeled target nucleic acid sequences, if present, within said mixture to thereby form and immobilize different fluorescent dye-labeled hybrids within said microtiter wells;
   removing non-hybridized fluorescent dye-labeled target nucleic acid sequences from within said microtiter wells;
   obtaining a specific combination filter set for spectrally distinguishing the fluorescence signal from each of the different fluorescent dye-labeled hybrids with a fluorescence reader instrument; and
   directly detecting and discriminating said different fluorescent dye-labeled hybrids within said microtiter wells with said fluorescence reader instrument.

2. The method described in claim 1 wherein said chemical linking means comprise covalent chemical linking means.

3. The method described in claim 1 wherein said chemical linking means comprise non-covalent chemical linking means.

4. The method described in claim 1 wherein one of said fluorescent dyes is bodipy and the specific combination filter set has an excitation center wavelength of 485 nm and an excitation bandwidth of 2.5 nm and an emission center wavelength of 510 nm and an emission bandwidth of 10 nm.

5. The method described in claim 1 wherein one of said fluorescent dyes is aminocoumarin and the specific combination filter set has an excitation center wavelength of 360 nm and an excitation bandwidth of 40 nm and an emission center wavelength of 460 nm and an emission bandwidth of 40 nm.

6. The method described in claim 1 wherein one of said fluorescent dyes is TET and the specific combination filter set has an excitation center wavelength of 525 nm and an excitation bandwidth of 5 nm and an emission center wavelength of 540 nm and an emission bandwidth of 5 nm.

7. The method described in claim 1 wherein one of said fluorescent dyes is TAMERA and the specific combination filter set has an excitation center wavelength of 555 nm and an excitation bandwidth of 5 nm and an emission center wavelength of 570 nm and an emission bandwidth of 6 nm.

8. The method described in claim 1 wherein one of said fluorescent dyes is Texas Red and the specific combination filter set has an excitation center wavelength of 600 nm and an excitation bandwidth of 5 nm and an emission center wavelength of 620 nm and an emission bandwidth of 10 nm.

9. The method described in claim 1 wherein one of said fluorescent dyes is Cy5 and the specific combination filter set has an excitation center wavelength of 640 nm and an excitation bandwidth of 10 nm and an emission center wavelength of 680 nm and an emission bandwidth of 20 nm.

10. A method for detecting and discriminating multiple target nucleic acid sequences, if present, within a mixture containing multiple target nucleic acid sequences resulting from a selective polymerase chain reaction amplification process, said method comprising the steps of:
   obtaining multiple primer oligonucleotides, each said primer oligonucleotide being complementary to a portion of one strand of a target nucleic acid sequence such that each said primer oligonucleotide can initiate amplification of a different target nucleic acid sequence in a polymerase chain reaction amplification process, said multiple target nucleic acid sequences including target nucleic acid sequences specific for microorganisms of the group consisting of Salmonella, Shigella, Campylobacter, Yersinia, and Escherichia coli;
   obtaining multiple probe oligonucleotides, each said probe oligonucleotide being complementary to a portion of one strand of one target nucleic acid sequence such that said probe oligonucleotides can form hybrids with said target nucleic acid sequences in a hybridization process;
   attaching multiple fluorescent dyes to either said primer oligonucleotides such that each said different target nucleic acid sequence resulting from said polymerase chain reaction amplification process is labeled with a different fluorescent dye or to said probe oligonucleotides such that each different target nucleic acid sequence/probe oligonucleotide hybrid is labeled with a different fluorescent dye;
   subjecting a sample to a polymerase chain reaction amplification process utilizing said primer oligonucleotides to thereby obtain a mixture of said multiple target nucleic acid sequences;
   obtaining a solid-phase system comprising a microtiter plate having microtiter wells and chemical linking means for efficiently binding said probe oligonucleotides to said microtiter wells;

effecting chemical linking of said probe oligonucleotides to said microtiter wells to thereby immobilize said probe oligonucleotides in said microtiter wells;

effecting hybridization of the probe oligonucleotides and the target nucleic acid sequences, if present, within said mixture to thereby form and immobilize different fluorescent dye-labeled hybrids within said microtiter wells;

removing non-hybridized fluorescent dye-labeled components from within said microtiter wells;

obtaining a specific combination filter set for spectrally distinguishing the fluorescence signal from each of the different fluorescent dye-labeled hybrids with a fluorescence reader instrument; and directly detecting and discriminating said different fluorescent dye-labeled hybrids within said microtiter wells with said fluorescence reader instrument.

11. A method for detecting and discriminating multiple target nucleic acid sequences, if present, within a mixture containing multiple target nucleic acid sequences resulting from a selective polymerase chain reaction amplification process, said method comprising the steps of:

obtaining a mixture of different fluorescent dye-labeled target nucleic acid sequences resulting from a selective polymerase chain reaction amplification process using multiple oligonucleotide primers labeled with multiple fluorescent dyes such that each different target nucleic acid sequence is labeled with a different fluorescent dye, said multiple target nucleic acid sequences including target nucleic acid sequences specific for microorganisms of the group consisting of *Salmonella*, *Shigella*, *Campylobacter*, *Yersinia*, and *Escherichia coli*;

obtaining multiple probe oligonucleotides, each said probe oligonucleotide being complementary to a portion of one strand of one target nucleic acid sequence such that said probe oligonucleotides can form hybrids with said fluorescent dye-labeled target nucleic acid sequences;

obtaining a solid-phase system comprising a microtiter plate having microtiter wells and chemical linking means for efficiently binding said probe oligonucleotides to said microtiter wells;

effecting chemical linking of said probe oligonucleotides to said microtiter wells to thereby immobilize said probe oligonucleotides in said microtiter wells;

effecting hybridization of the probe oligonucleotides and the fluorescent dye-labeled target nucleic acid sequences, if present, within said mixture to thereby form and immobilize different fluorescent dye-labeled hybrids within said microtiter wells;

removing non-hybridized fluorescent dye-labeled target nucleic acid sequences from within said microtiter wells;

obtaining a specific combination filter set for spectrally distinguishing the fluorescence signal from each of the different fluorescent dye-labeled hybrids with a fluorescence reader instrument; and directly detecting and discriminating said different fluorescent dye-labeled hybrids within said microtiter wells with said fluorescence reader instrument.

12. The method described in claim 11 wherein said solid-phase system comprises a microtiter plate having covalent chemical linking means for efficiently binding hybrid molecules.

13. The method described in claim 11 wherein one of said fluorescent dyes is bodipy and the specific combination filter set has an excitation center wavelength of 485 nm and an excitation bandwidth of 2.5 nm and an emission center wavelength of 510 nm and an emission bandwidth of 10 nm.

14. The method described in claim 11 wherein one of said fluorescent dyes is aminocoumarin and the specific combination filter set has an excitation center wavelength of 360 nm and an excitation bandwidth of 40 nm and an emission center wavelength of 460 nm and an emission bandwidth of 40 nm.

15. The method described in claim 11 wherein one of said fluorescent dyes is TET and the specific combination filter set has an excitation center wavelength of 525 nm and an excitation bandwidth of 5 nm and an emission center wavelength of 540 nm and an emission bandwidth of 5 nm.

16. The method described in claim 11 wherein one of said fluorescent dyes is TAMERA and the specific combination filter set has an excitation center wavelength of 555 nm and an excitation bandwidth of 5 nm and an emission center wavelength of 570 nm and an emission bandwidth of 6 nm.

17. The method described in claim 11 wherein one of said fluorescent dyes is Texas Red and the specific combination filter set has an excitation center wavelength of 600 nm and an excitation bandwidth of 5 nm and an emission center wavelength of 620 nm and an emission bandwidth of 10 nm.

18. The method described in claim 11 wherein one of said fluorescent dyes is Cy5 and the specific combination filter set has an excitation center wavelength of 640 nm and an excitation bandwidth of 10 nm and an emission center wavelength of 680 nm and an emission bandwidth of 20 nm.

19. The method described in claim 11 wherein the step of obtaining multiple probe oligonucleotides comprises obtaining oligonucleotide sequences from the group consisting of SEQ ID NO: 1 through SEQ ID NO: 9.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TGGTTGATTT CCTGATCGC                                                 1 9

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GCGATCAGGA AATCAACCA                                                 1 9

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTGATCAGAT AAGGAAGATT G                                             2 1

( 2 ) INFORMATION FOR SEQ ID NO:4:

(i) SEQUENCE CHARACTERISTICS:
   (A) LENGTH: 21 base pairs
   (B) TYPE: nucleic acid
   (C) STRANDEDNESS: single
   (D) TOPOLOGY: linear (ii) MOLECULE TYPE: DNA (xi) SEQUENCE DESCRIPTION: SEQ ID NO:4:

CAATCTTCCT TATCTGATCA G                                                  21

(2) INFORMATION FOR SEQ ID NO:5:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:5:

AAACTTGGAA CACTTCTTGC T                                                  21

(2) INFORMATION FOR SEQ ID NO:6:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:6:

AGCAAGAAGT GTTCCAAGTT T                                                  21

(2) INFORMATION FOR SEQ ID NO:7:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:7:

TGTGTACGCT GCGAGTGAAA                                                    20

(2) INFORMATION FOR SEQ ID NO:8:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:8:

TGGAATTGAG CAGCGTTG                                                      18

(2) INFORMATION FOR SEQ ID NO:9:

(i) SEQUENCE CHARACTERISTICS:
      (A) LENGTH: 20 base pairs
      (B) TYPE: nucleic acid
      (C) STRANDEDNESS: single -continued ( D ) TOPOLOGY: linear ( i i ) MOLECULE TYPE: DNA ( x i ) SEQUENCE DESCRIPTION: SEQ ID NO:9:

CAACTTCATC CACGTTCACC 20